(12) United States Patent
Webber

(10) Patent No.: US 7,078,577 B2
(45) Date of Patent: Jul. 18, 2006

(54) DIHYDRODICYCLOPENTADIENE PRODUCTION

(75) Inventor: Kenneth M. Webber, Friendswood, TX (US)

(73) Assignee: Equistar Chemicals, LP, Houston, TX (US)

( * ) Notice: Subject to any disclaimer, the term of this patent is extended or adjusted under 35 U.S.C. 154(b) by 470 days.

(21) Appl. No.: 10/638,601

(22) Filed: Aug. 11, 2003

(65) Prior Publication Data

US 2005/0038303 A1  Feb. 17, 2005

(51) Int. Cl.
*C07C 5/02* (2006.01)
*C07C 5/05* (2006.01)

(52) U.S. Cl. .................. 585/275; 585/277; 585/273; 585/271; 585/261; 585/259; 585/260

(58) Field of Classification Search .............. 585/277, 585/275, 273, 271, 261, 259, 260
See application file for complete search history.

(56) References Cited

U.S. PATENT DOCUMENTS 3,489,809 A    1/1970  Keith et al. ................ 260/677
3,691,066 A  *  9/1972  Carruthers et al. ......... 208/255

FOREIGN PATENT DOCUMENTS

GB         848232      *  9/1960

* cited by examiner

*Primary Examiner*—Walter D. Griffin
(74) *Attorney, Agent, or Firm*—Roderick W. MacDonald

(57) ABSTRACT

A method for forming dihydroDicyclopentadiene comprises mixing a source of dicyclopentadiene with at least one solvent and at least one reactive component in the presence of a source of hydrogen and a selective hydrogenation catalyst, the solvent and reactive component being readily separable from dihydroDicyclopentadiene, and the reactive component and catalyst favoring the formation of dihydroDicyclopentadiene over tetra hydro dicyclopentadiene.

13 Claims, No Drawings

DIHYDRODICYCLOPENTADIENE PRODUCTION

BACKGROUND OF THE INVENTION

1. Field of the Invention

This invention relates to a method for making dihydroDicyclopentadiene by employing selective hydrogenation of dicyclopentadiene.

2. Description of the Prior Art

Cyclopentadiene (CPD) is a known 5 carbon atom diolefin. CPD is not stable and spontaneously converts to dicyclopentadiene (DCPD), a known 10 carbon atom diolefin. Such conversion occurs naturally even at room temperature and ambient pressure. DihydroDCPD is the monounsaturated (monoolefin) form of DCPD. TetrahydroDCPD is the saturated form of DCPD, and therefore contains no double bonds or other unsaturation.

DCPD is also not stable, and tends to combine with itself and form higher molecular weight compounds known as "gums." When such gums form in an automotive gasoline stream, they can make the stream miss its required specification for motor gasoline.

DCPD can be hydrotreated to remove one or both of the double bonds therein that make it so reactive with itself. However, it is commercially desirable to separate the DCPD as itself because, as will be described hereinafter, DCPD has valuable uses of its own.

Thermal cracking of hydrocarbons is a petrochemical process that is widely used to produce a variety of olefins and aromatics. In an olefin/aromatic production plant using thermal cracking, a hydrocarbon feedstock such as naphtha, gas oil, or other fractions of whole crude oil is mixed with steam which serves as a diluent to keep hydrocarbon molecules separated. This mixture, after preheating, is subjected to severe hydrocarbon thermal cracking (pyrolysis) at elevated temperatures (1,450 to 1,550° F.) in a pyrolysis furnace (steam cracker).

The cracked effluent product from this pyrolysis process contains gaseous hydrocarbons of great variety (from 1 to 35 carbon atoms per molecule). This effluent contains hydrocarbons that are aliphatic, aromatic, saturated, and unsaturated, including a substantial amount of CPD which rapidly forms DCPD on its own under the various conditions prevalent in an olefin/aromatic production plant. Thus, such hydrocarbon cracking processes are a significant source of commercial amounts of DCPD.

The cracked product of a pyrolysis furnace is then further processed in the plant to produce, as products of the plant, various separate individual product streams of high purity such as hydrogen, ethylene, propylene, mixed hydrocarbons having 4 carbon atoms per molecule (crude C4's), and a mixture of hydrocarbons in the gasoline boiling range which are collectively known as pyrolysis gasoline (pygas). The DCPD formed in a conventional steam cracking plant typically ends up in the pygas stream.

DCPD in the pygas stream can be partially hydrogenated to its dihydroDCPD monoolefin form. However, it is virtually impossible commercially to separate the dihydroDCPD from the other hydrocarbons in the pygas because there are a large number of other molecular structures in the pygas mixture that have a similar or identical separation characteristics, e.g., boiling point, as dihydroDCPD.

DCPD can be readily concentrated when present in a hydrocarbon mixture such as pygas, e.g., C8 to 400° F. end point, by thermally back-cracking the DCPD to CPD, and then distilling the CPD off from the hydrocarbon mixture under conditions such that the CPD is rapidly removed as an overhead vapor. The thus concentrated CPD distillate readily and rapidly recombines with itself on its own to form a mixture containing primarily DCPD with a minor amount of unreacted CPD. Back-cracking is the prior art way of commercially concentrating DCPD, i.e., forming a high purity DCPD product useful in other commercial chemical applications.

DihydroDCPD is more difficult to concentrate by back-cracking than DCPD because once back-cracked, dihydroDCPD does not recombine on its own to reform dihydroDCPD. This is because back-cracking of dihydroDCPD forms cyclopentene and CPD, and cyclopentene is not a reactive diene compound.

DCPD can be used for producing cross-linked resins since it is a diene. Partial hydrogenation of concentrated DCPD yields the monoolefin dihydroDCPD which is a valued precursor in the fragrance industry as well as being useful as a monomer or comonomer for making polymers such as low density polyethylene or for ring opening metathesis operations, all of which are different from the cross linked resin uses for DCPD.

Thus, although DCPD has commercial uses of value, dihydroDCPD is an upgraded product from DCPD that has other valuable uses that cannot be accomplished with DCPD.

Partial hydrogenation of concentrated DCPD made by the aforesaid back-cracking process is very difficult to achieve because it tends to form a significant amount of the undesired saturated tetrahydroDCPD. Hydrogenation of DCPD is an exothermic reaction. The heat released during the hydrogenation of the first double bond in a DCPD molecule will cause a significant increase in temperature of the reaction mixture. At higher temperatures, the hydrogenation of the remaining second double bond in the DCPD molecule is more favorable than at lower temperatures.

It was theorized that if DCPD was partially hydrogenated to dihydroDCPD in the presence of an inert solvent, a lower temperature rise would be experienced in the hydrogenation reactor and the formation of tetra hydro DCPD would thereby largely be avoided.

It was surprisingly found that selective hydrogenation of DCPD to dihydroDCPD was negligible (0.2 weight percent based on the total weight of the reaction mixture) when such an inert solvent (toluene and/or isooctane) was used.

SUMMARY OF THE INVENTION

Even more surprisingly, it was found that when certain reactive components were employed in conjunction with an inert solvent the selective hydrogenation of DCPD to dihydroDCPD was almost quantitative (99.8 weight percent based on the total weight of the reaction mixture).

DETAILED DESCRIPTION OF THE INVENTION

In accordance with this invention, a source of DCPD such as concentrated DCPD, is mixed with at least one inert solvent that is deliberately chosen for its ready separability from DCPD and at least one reactive component as hereinafter described that promotes the formation of dihydroDCPD over tetra hydro DCPD and which also is deliberately chosen for its ready separability from DCPD. The resulting mixture is contacted under reaction conditions with a source of hydrogen and at least one selective hydrogenation catalyst that favors the selective hydrogenation of only one double bond in a diolefin compound.

The source of DCPD can be any source that contains a significant concentration of DCPD. It can be pure DCPD, concentrated DCPD, or a mixture of DCPD and other hydrocarbons so long as such hydrocarbons are readily separable from dihydroDCPD in the same manner as the inert solvent and reactive component used.

The inert solvent is deliberately selected to be non-reactive under the selective hydrogenation reaction conditions and in the presence of the hydrogenation catalyst or catalysts employed in the reaction. The solvent is also deliberately chosen so as to be readily separated from dihydroDCPD by subsequent processing, such as distillation, crystallization, liquid-liquid extraction, and the like, of the reaction product mixture. The amount of solvent used will vary widely, but will generally be that amount which keeps the temperature of the reaction mixture from rising to a point that favors the formation of tetra hydro DCPD and thereby prevent the formation of significant amounts of tetra hydro DCPD in the reaction product mixture. Generally, the amount of solvent added to the DCPD present will be from about 10 weight percent to about 400 weight percent, preferably from about 25 weight percent to about 200 weight percent, all weight percents being based on the total weight of DCPD, solvent, and reactive component present and including any oligomers of CPD higher than DCPD (e.g., trimmers and tetramers of CPD) and reaction products of CPD with diolefins (butadiene and isoprene) that may be found in the mixture.

By the terms "readily separated," "readily separable," and the like in reference to this invention, what is meant is a material at least one of whose physical and/or chemical characteristics allows substantial if not essentially complete separation of the dihydroDCPD product from the solvent(s) and reactive component(s) present in the reaction mixture product. Such characteristics can be relative boiling points, crystallization points, liquid extraction capabilities, or any number of other characteristics which allow significant, substantial, and prompt removal of dihydroDCPD from the solvent(s) and reactive component(s). For example, when distillation is the chosen separating process for the dihydroDCPD from the reaction mixture, a boiling point difference between dihydroDCPD on the one hand and the solvent and reactive component(s) on the other hand of at least 2° F. makes the dihydroDCPD readily separable from the solvent and reactive component. Such a distillation with one or more of the solvents and reactive components listed here in below can be carried out in a temperature range of from 50 to about 400° F. at a pressure of from about atmospheric to about 50 psig. A distillation temperature of from about 50 to about 150° F. could particularly be used because the lower the distillation temperature, the less likely the dihydroDCPD will be back-cracked. Also, the lower the distillation pressure used, the less the likelihood of back-cracking the dihydroDCPD present. Similarly, a crystallization temperature difference of at least 10° F. achieves ready separability of dihydroDCPD from the reaction product mixture for the purposes of this invention.

The inert solvent can vary widely within the above parameters, suitable such solvents being alkanes having from 3 to 8, inclusive, carbon atoms per molecule (both linear and branched chain alkanes), benzene, toluene, and mixtures of two or more thereof.

Specific solvents include benzene, toluene, propane, butane, pentane, 2-methylbutane, hexane, 2 methylpentane, 3-methylpentane, cyclohexane and methylcyclohexane The reactive component can be at least one compound selected from monoolefins (linear or branched, alpha or internal) having from 2 to 9, inclusive, carbon atoms per molecule; diolefins (linear or branched with terminal double bonds, internal double bonds, or a combination thereof) having from 3 to 9, inclusive, carbon atoms per molecule; acetylenes (linear or branched with terminal double bonds, internal double bonds, or a combination thereof) having from 2 to 9, inclusive, carbon atoms per molecule; acetylenes with olefin linkages having from 4 to 9, inclusive, carbon atoms per molecule; ketones having from 1 to 7, inclusive, carbon atoms per molecule; aldehydes having from 1 to 7, inclusive, carbon atoms per molecule; alcohols having from 1 to 6, inclusive, carbon atoms per molecule, and mixtures of two or more thereof. Particular components are monoolefins having 3 to 9, inclusive, carbon atoms per molecule; diolefins having 4 or 5 carbon atoms per molecule; acetylenes having 2 to 5, inclusive, carbon atoms per molecule; and acetylenes with olefinic linkages having 4 or 5 carbon atoms per molecule. Still more particular components are monoolefins having 4 or 5 carbon atoms per molecule, diolefins having 4 or 5 carbon atoms per molecule, and vinylacetylene.

Suitable specific reactive components include ethylene, propylene, normal butene-1 or -2, isobutene, butadiene, vinylacetylene, isoprene, piperylene, normal pentene-1 or -2, 2-methyl butene-1 or -2, 3-methyl butene-1, vinylcyclohexane, vinylcyclohexene or styrene The amount of reactive component or components used in total will vary widely, but will generally be from about 1 to about 100, particularly from about 5 to about 50 weight percent based on the total weight of DCPD, solvent, and reactive component present and including oligomers of CPD and higher than DCPD and reaction products of CPD with diolefins that may be found in the mixture.

The catalyst employed to promote the selective hydrogenation of DCPD to dihydroDCPD with the formation of minimal amounts of tetrahydroDCPD can be any catalyst that favors or is otherwise primarily selective to the hydrogenation of a single double bond in a diolefinic compound like DCPD as opposed to the hydrogenation of both double bonds in such a compound. Suitable such catalysts include platinum, palladium, and nickel. The catalyst may be employed in a supported or unsupported form. Suitable supports include alumina, silica, carbon, and zeolite. The amount of catalyst employed will vary widely depending on the make up of the reactive mixture, but will generally be an amount sufficient to promote the selective hydrogenation of a single double bond in a diolefin compound such as DCPD. A suitable, supported or otherwise, catalyst will contain from about 0.03 to about 50 weight percent catalytic material based on the total weight of the catalyst. Such catalysts are known in the art and commercially available and further detail is not necessary to inform the art, see U.S. Pat. No. 3,489,809.

The reaction conditions for the mixture of DCPD, solvent, and reactive component in the presence of the selective hydrogenation catalyst will also vary widely, but will be that which favors the desired selective hydrogenation results aforesaid. Generally, such conditions will be a temperature of from about 100 to about 400° F., particularly from about 120 to about 300° F.; a pressure of from about atmospheric to about 600 psig, particularly from about 100 to about 500 psig; and a weight hourly space velocity of from about 0.5 to about 10, particularly from about 1 to about 6, reciprocal hours ($h^{-1}$).

In the process of this invention the DCPD converts primarily (at least about 80% by weight based on the total weight of the DCPD in the initial reaction mixture) to dihydroDCPD with the remainder being essentially minor amounts (no more than about 20% by weight based on the total weight of the DCPD in the initial reaction mixture) tetra hydro DCPD. Depending on the availability of hydrogen and other considerations, any reactive component diolefin such as butadiene that may be present could be hydrogenated at least in part to a monoolefin such as butenes, and monoolefins such as butenes hydrogenated at least in part to alkanes such as butanes during the process of this invention. Such hydrogenation products are also readily separable from dihydroDCPD as are the solvents and reactive components described hereinabove. At least about 80 weight percent, based on the total weight of the reaction product, of the dihydroDCPD in the resulting reaction mixture can be separated from that reaction mixture by distillation or the like as aforesaid to form a high purity dihydroDCPD product useful commercially in the fragrance industry and the like also as aforesaid.

EXAMPLE 1

A tubular reactor was loaded with 9.0 grams of a selective hydrogenation catalyst consisting essentially of 0.4 weight percent (wt. %) palladium, based on the total weight of the catalyst, on alumina. A feed mixture was prepared by blending isooctane, toluene, and DCPD to give a composition containing the following, the remainder being various hydrocarbon impurities:

| Component | Concentration, Wt % Based on the total weight of the blend |
| --- | --- |
| Isooctane | 32.2 |
| Toluene | 34.2 |
| DCPD | 32.7 |
| DihydroDCPD | 0 |
| TetrahydroDCPD | 0 |

This mixture was fed continuously at 20 grams per hr along with 40 sccm (standard cubic centimeters per minute) to the reactor at 407 psig. The blended stream was preheated to 177° F. before entering the catalyst bed. The product effluent from the reactor was analyzed and determined to contain the following composition excluding the various hydrocarbon impurities:

| Component | Concentration, Wt % Based on the total weight of the blend |
| --- | --- |
| Isooctane | 32.2 |
| Toluene | 34.0 |
| DCPD | 32.6 |
| DihydroDCPD | 0.1 |
| TetrahydroDCPD | 0 |

With this solvent mixture, only about 0.2 Wt %, based on the total product effluent, of the DCPD was hydrogenated to dihydroDCPD.

EXAMPLE 2

The same catalyst loading as used in Example-1 was used for a second run. For this run DCPD was mixed with a $C_4$ stream (a raffinate stream from an olefin steam cracking operation) to give a feed mixture of the following composition containing the following, the remainder is being various hydrocarbon impurities:

| Component | Concentration, Wt % Based on the total weight of the blend |
| --- | --- |
| Butanes | 13.0 |
| Butenes | 49.2 |
| 1,3 Butadiene | 0.5 |
| DCPD | 34.5 |
| DihydroDCPD | 0 |
| TetrahydroDCPD | 0 |

This mixture was fed continuously at 22 gram per hr along with 40 sccm (standard cubic centimeters per minute) to the reactor at 409 psig. The blended stream was preheated to 170° F. before entering the catalyst bed. The product effluent from the reactor was analyzed to and determined to contain the following composition excluding the various hydrocarbon impurities:

| Component | Concentration, Wt % Based on the total weight of the blend |
| --- | --- |
| Butanes | 24.6 |
| Butenes | 39.9 |
| 1,3 Butadiene | 0 |
| DCPD | 0.1 |
| DihydroDCPD | 28.1 |
| TetrahydroDCPD | 5.2 |

The change in feed mixture resulted in over 99 Wt % of the DCPD being converted to hydrogenated products, with about 84% of the hydrogenated DCPD being the partially hydrogenated dihydroDCPD and the remainder being essentially the fully saturated tetrahydroDCPD.

EXAMPLE 3

The same catalyst loading as used in the previous two examples was used for a third run. For this run DCPD was mixed with a second $C_4$ stream (a hydrotreated raffinate stream from an olefin steam cracking operation) to give a feed mixture of the following composition containing the following, the remainder is being various hydrocarbon impurities:

| Component | Concentration, Wt % Based on the total weight of the blend |
| --- | --- |
| Butanes | 13.9 |
| Butenes | 50.2 |
| 1,3 Butadiene | 0 |
| DCPD | 30.1 |
| DihydroDCPD | 0 |
| TetrahydroDCPD | 0 |

This mixture was fed continuously at 29 grams per hour along with 40 sccm (standard cubic centimeters per minute) to the reactor at 396 psig. The blended stream was preheated to 168° F. before entering the catalyst bed. The product effluent from the reactor was analyzed and determined to contain the following composition excluding the various hydrocarbon impurities:

| Component | Concentration, Wt % Based on the total weight of the blend |
|---|---|
| Butanes | 44.8 |
| Butenes | 21.3 |
| 1,3 Butadiene | 0 |
| DCPD | <0.1 |
| DihydroDCPD | 29.5 |
| TetrahydroDCPD | 1.0 |

The change in feed mixture resulted in over 99 Wt % of the DCPD being converted to hydrogenated products, with about 97% of the hydrotreated DCPD being the partially hydrogenated dihydroDCPD and the remainder being essentially the fully saturated tetrahydroDCPD.

Reasonable variations and modifications are possible within the scope of this disclosure without departing from the spirit and scope of this invention.

I claim:

1. A method for the selective catalytic hydrogenation of dicyclopentadiene to dihydroDicyclopentadiene comprising providing a source of dicyclopentadiene, adding to said source at least one solvent that is inert in the presence of the catalyst employed and that is readily separable from dihydroDicyclopentadiene, additionally adding to said source at least one reactive component that promotes the hydrogenation of dicyclopentadiene to dihydroDicyclopentadiene preferentially over tetra hydro dicyclopentadiene and is readily separable from dihydrodicyclopentadiene, said reactive component being at least one compound selected from the group consisting essentially of acetylenes having from 2 to 9, inclusive, carbon atoms per molecule; acetylenes with olefinic linkages having from 4 to 9, inclusive, carbon atoms per molecule; ketones having from 1 to 7, inclusive, carbon atoms per molecule; aldehydes having from 1 to 7, incluse, carbon atoms per molecule; and alcohols having from 1 to 6, inclusive, carbon atoms per molecule; said solvent being employed in an amount such that the formation of dihydroDicyclopentadiene is favored over that of tetra hydro dicyclopentadiene, and contacting the resulting mixture under reaction conditions with a source of hydrogen and at least one selective hydrogenation catalyst that favors the selective hydrogenation of only one double bond in a diolefin compound.

2. The method of claim 1 wherein said solvent is at least one compound selected from the group consisting essentially of alkanes having from 3 to 8, inclusive, carbon atoms per molecule, benzene, and toluene.

3. The method of claim 1 wherein said alkanes are at least one of linear and branched.

4. The method of claim 1 wherein said selective hydrogenation catalyst is at least one material selected from the group consisting essentially of platinum, palladium, and nickel.

5. The method of claim 4 wherein said catalyst is supported on at least one of alumina, silica, carbon, and zeolite.

6. The method of claim 1 wherein said reaction conditions are a temperature of from about 100 to about 400° F., a pressure of from about atmospheric to about 600 psig, and a weight hourly space velocity of from about 0.5 to about 10 $h^{-1}$.

7. The method of claim 1 wherein said reactive component is at least one compound selected from the group consisting essentially of acetylenes having from 2 to 5, inclusive, carbon atoms per molecule; and acetylenes with olefinic linkages having 4 or 5 carbon atoms per molecule.

8. The method of claim 1 wherein said reactive component is vinyl acetylene.

9. The method of claim 1 wherein the dihydroDicyclopentadiene formed in said mixture is separated from said mixture by one of distillation, crystallization, and liquid-liquid extraction.

10. The method of claim 9 wherein said dihydroDicyclopentadiene is separated by distillation in a temperature range of from about 50 to about 400° F., under a pressure of from about atmospheric to about 50 psig.

11. The method of claim 1 wherein said inert solvent and reactive component have a boiling point at least about 2° F. higher than the boiling point of dihydroDicyclopentadiene.

12. The method of claim 1 wherein said inert solvent and reactive component have a crystallization temperature at least 10° F. different from dihydroDicyclopentadiene.

13. The method of claim 1 wherein the amount of solvent employed is from about 10 to about 400 weight percent based on the total weight of dicyclopentadiene and oligomers and reaction products thereof, solvent, and reactive component present; and the amount of reactive component employed in total is from about 1 to about 100 weight percent based on the total weight of dicyclopentadiene and oligomers and reaction product thereof, solvent, and reactive component.

* * * * *